United States Patent [19]

Horn et al.

[11] 4,119,589
[45] Oct. 10, 1978

[54] PROCESS FOR FIXING PROTEINS ONTO CARRIERS

[75] Inventors: Jürgen Horn, Tutzing, Garatshausen; Hans-Georg Batz, Tutzing, Obb.; Dieter Jaworek, Weilheim, all of Germany

[73] Assignee: Boehringer Mannheim GmbH, Mannheim-Waldhof, Germany

[21] Appl. No.: 760,296

[22] Filed: Jan. 18, 1977

[30] Foreign Application Priority Data

Jan. 29, 1976 [DE] Fed. Rep. of Germany ....... 2603319

[51] Int. Cl.² .............................................. C08L 89/00
[52] U.S. Cl. .......................................... 260/6; 195/63; 195/68; 260/8; 260/112 R; 424/12; 424/177
[58] Field of Search ................... 260/6, 112 R

[56] References Cited

U.S. PATENT DOCUMENTS

| | | | |
|---|---|---|---|
| 3,639,558 | 2/1972 | Csizmas | 424/12 |
| 3,806,417 | 4/1974 | Beaucamp | 260/112 R |
| 3,959,079 | 5/1976 | Mareschi et al. | 195/63 |
| 3,970,597 | 7/1976 | Sokolovsky | 195/63 |
| 3,985,617 | 10/1976 | Yugari et al. | 260/112 R |
| 4,007,089 | 2/1977 | Smith | 260/112 R |
| 4,045,384 | 8/1977 | Dorman | 260/8 |

*Primary Examiner*—Edward M. Woodberry
*Attorney, Agent, or Firm*—Burgess, Dinklage & Sprung

[57] ABSTRACT

Biologically active proteins are immobilized onto a carrier by reacting a compound containing at least two secondary amino groups at a temperature of from −80° to +50° C with a chlorination agent with the conversion of the secondary amino groups into iminochloride groups of the formula

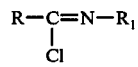

in which R and $R_1$, which can be the same or different, are aliphatic, aromatic or aliphatic-aromatic radicals, and reacting the carrier material product thus obtained
(a) directly with a biologically-active protein, in an aqueous solvent, or
(b) with a bifunctional compound containing at least one primary amino group, optionally in an aqueous or organic solvent, and reacting the product thereby obtained containing groups of the formula

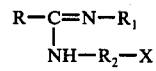

in which $R_2$ is an alkylene radical, an α,ω-dioxyalkylene radical or a dicarboxylic acid amide group containing 2 to 8 carbon atoms and X is a primary amino group or a function capable of protein binding either
(i) directly with a protein or
(ii) first with at least one bifunctional or polyfunctional protein reagent and thereafter with a protein or with a reaction product of a protein with the protein reagent.

13 Claims, No Drawings

PROCESS FOR FIXING PROTEINS ONTO CARRIERS

The present invention is concerned with a process for fixing proteins, especially biologically active proteins, on to liquid or solid carrier materials.

The fixing or immobilizing of biologically-active proteins, such as enzymes, hormones, substances capable of participating in antigen-antibody reactions and haptene antibody reactions, coagulation factors and the like, especially in the field of preparative and analytical chemistry, has achieved great importance in recent years. Numerous fixing processes have already been developed. Nevertheless, it has been found that new fixing problems constantly arise and that these cannot be satisfactorily solved with the previously known methods. This is also the reason why hitherto, in spite of the clearly foreseeable advantages of fixing biologically-active proteins on to carrier materials, in many fields the introduction of fixed proteins has only taken place slowly in actual practice and the expected wide breakthrough has not yet been realized.

Furthermore, most methods of immobilization can only be used for particular carrier materials or require the production of the carrier by polymerization from aqueous solution in the presence of biologically-active proteins (protein copolymerization) which also severely limits the carrier materials which can be used.

Of special interest as carrier materials for immobilized active proteins would be substances which contain secondary amino groups. To these belong, on the one hand, various polymers which are characterized by especially favorable mechanical and chemical properties, for example polyamides and polyurethanes, and on the other hand, polypeptide-like structures, such as polyamino acids and the like. Such substances with secondary amino groups have a certain chemical similarity with protein structures, especially with regard to their charge distribution, so that here an adverse action upon the biological activity of the enzymes immobilized thereon are not to be expected or can be expected to remain small insofar as no other groups are present which act especially disadvantageously upon the activity of proteins.

It is already known that imido esters, which can be easily obtained from secondary amines, react specifically with the amino groups of proteins with the formation of amidino structures (cf., for example Colowick-Kaplan, "Methods in Enzymology", vol. 25 pp 646-648). It is also known that polyamides can be converted into polyimino esters with the use of strong alkylation agents (see U.S. Pat. No. 3,340,210). However, an important disadvantage of such imino esters for protein fixing is that they are soluble or at least swellable in solvents. This results in a very considerable stickiness which makes difficult or even impossible especially the working with granulates, foils, tubes and similar formed bodies because of the adhesion which occurs.

The present invention provides a process which enables biologically-active proteins to be fixed, while maintaining their activity, and which does not display the above-mentioned disadvantages of the known processes.

Essentially, in the present invention, proteins are fixed onto substances which contain at least two secondary amino groups.

More specifically, according to the present invention, there is provided a process for immobilizing biologically-active proteins, comprising reacting a compound containing at least two secondary amine groups at a temperature of from $-80°$ to $+50°$ C. with a chlorination agent with the conversion of the secondary amino groups into imino-chloride groups of the general formula:

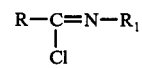

in which R and $R_1$, which can be the same or different, are aliphatic, aromatic or aliphatic-aromatic radicals, and reacting the carrier material product thus obtained
 (a) directly with a biologically-active protein, in an aqueous solvent, or
 (b) with a bifunctional compound containing at least one primary amino group, optionally in an aqueous or organic solvent, and reacting the product thereby obtained containing groups of the general formula:

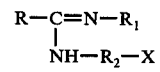

(in which R and $R_1$ are defined as above, $R_2$ is alkylene, $\alpha,\omega$-dioxyalkylene or a dicarboxylic acid amide group containing 2 to 8 carbon atoms and X is a primary amino group or a function capable of protein binding) either
 (i) directly with a protein or
 (ii) first with at least one bifunctional or polyfunctional protein reagent and thereafter with a protein or with a reaction product of a protein with the protein reagent.

The imino-chlorination reaction according to the present invention is preferably carried out on liquid or solid polymers which contain secondary amino groups. Of these, the polyamides, such as nylon, perlon and the like, are especially preferred. Polyurethane is another example of a polymer containing secondary amino groups.

In the case of solid polymers containing secondary amino groups, it can be advisable to subject the polymers to the reaction according to the present invention in a dissolved state. For this purpose, there can be used the conventional solvents which are well known for the polymers in question. If the polymer containing the secondary amino groups is present in a solid state, then it can be in the form of powder or of a solid body, for example a tube or the like. In the case of formed bodies with a relatively small surface area in relation to the mass, it can be advisable to activate the surface area intended for the reaction. The activation preferably takes place by deposition of a finely-divided polymer from a solution thereof. For example, polyamides such as nylon can be dissolved in the solvents conventional therefor and then deposited in a finely-divided, amorphous and thus more reactive form on the surface of a synthetic resin formed body.

In an analogous manner, it is also possible to apply coatings of polymers which contain secondary amino groups to formed bodies which do not consist of polymers containing secondary amino groups. Again, this advantageously takes place by deposition of these polymers in active form from solutions thereof. However, if desired, it is also possible to use conventional techniques for applying coatings, such as extruding on, application of liquids, melting on, applying films and the like.

However, the present invention is not limited to polymers but is quite generally applicable to all compounds which can be considered as carriers for biologically-active proteins and which contain a plurality of secondary amine groups, for example peptides.

A preferred chlorination agent for the preparation of the imino chloride is phosphorus pentachloride. Other chlorination agents which can be used include, for example, phosphorus trichloride, thionyl chloride, phosgene, phosphorus oxychloride and sulphuryl chloride. The two latter agents are admittedly not so reactive as phosphorus pentachloride but, in comparison therewith, have the advantage of being liquid so that they can be employed without the use of a solvent. However, in the case of phosphorus pentachloride, it is necessary to use a solvent. Appropriate solvents include, for example, halogenated solvents, such as dichloroethane, methylene chloride, chloroform, carbon tetrachloride and the like. According to an especially preferred embodiment, the preparation of the imino-chloride is carried out with the use of phosphorus pentachloride in dichloroethane at a temperature of from $-38°$ to $0°$ C. These preferred conditions can easily be achieved by the addition of solid carbon dioxide to the dichloroethane solution or to the solution in another halogenated solvent. Other methods of cooling can, of course, also be employed.

After completion of the reaction, excess chlorination agent is preferably removed before carrying out the reaction with the diamine. However, as an alternative, it is also possible, without previous removal of residual chlorination agent, to add directly the bifunctional compound containing at least one primary amino group insofar as no direct bonding is to take place with the biologically active protein. If the chlorination agent is not removed before the addition of the bifunctional compound, then a reaction can take place between excess chlorination agent and the bifunctional compound. If, for example, the bifunctional compound used is a diamine, then excess halogenation agent can react with the second free amino group. If such an intermediate product is reacted directly with the protein, then the groups formed by the reaction of the residual chlorination agent with the free function of the bifunctional compound also react with the protein. If, for example, phosphorus pentachloride is used as chlorination agent and, after the reaction with the formation of the imino-chloride excess chlorination agent is not removed, then the enzyme is bound, via condensed on phosphoric acid chloride groups, on to the free amino group of the diamine. We have ascertained that, even under these conditions, high yields of biological activity can be obtained in the case of the protein fixing (cf. the following Example 8).

R and $R_1$, which can be the same or different, are aliphatic, aromatic or aliphatic-aromatic radicals which can contain further secondary and tertiary amino groups, ester groups, amide groups, sulphhydryl groups, carboxyl groups, hydroxyl groups and/or imino-chloride groups. R and $R_1$ preferably signify straight-chained, branched and/or cyclic alkyl radicals or alkylene radicals containing up to 12 carbon atoms, phenyl radicals or phenylene radicals or alkyl-phenyl radicals or alkylene-phenyl radicals containing up to 6 carbon atoms in the alkyl radical, which are joined together by one or more of the above-mentioned amino groups, ester groups, amide groups and/or imino-chloride groups, peptide chains of natural and/or synthetic amino acids or the like. Typical examples of compounds which, according to the present invention, can be coupled with biologically-active proteins via the formation of imino-chloride groups include 6-polyamide, 6,6-polyamide, 6,10-polyamide, 11-polyamide, 12-polyamide, polycyclamides, such as poly-(1,4-cyclohexylenedimethylene-supramide), polydodecanol lactam, wool, casein, natural silk, polyarginino and the like. Amongst the synthetic polymers, those are preferred in which R and $R_1$ are alkylene and cycloalkylene radicals with 6 to 12 carbon atoms which are joined together by amide groups.

According to the present invention, the imino-chloride can be reacted directly in an aqueous solvent with the biologically-active protein. The biologically-active protein is thereby preferably dissolved in an appropriate aqueous buffer, mixed with the solid imino-chloride and left to react. Such a method of working is to be especially recommended when the base structure of the imine is branched, for example in the case of polyamides which contain components with 3, 4 or more functions. Due to the steric relationships which thereby arise, the direct reaction between the imino-chloride and the protein is favoured. In the case of straight-chained polymers, on the other hand, the reaction with the proteins preferably takes place via an intermediate compound which contains at least one primary amino group (spacer).

The primary amino group can be connected directly with a carbon atom or can be present as a hydrazide group, i.e. is present bound to an acid amide group. If two primary amino groups are present, then the two amino groups are preferably separated from one another by an alkylene, $\alpha,\omega$-dioxyalkylene or dicarboxylic acid amide group containing 2 to 8 carbon atoms.

If, instead of a diamide, a monoamide is used, then this contains a further functional group which is preferably a group capable of forming a bond with a protein. This second functional group of the intermediate compound, regardless of whether it is a primary amino group or some other group, can be further reacted with a bifunctional protein reagent. Such compounds include, for example, dialdehydes, such as glutardialdehyde, dihydroxy-succinimide esters, diacetals, bismaleinimides, bi-functional imino esters, such as diethyl malonimidate, dimethyl adipinimidate, diepoxides, dicarboxylic acid acid chlorides, especially $\alpha,\beta$-unsaturated dicarboxylic acid dichlorides, diisocyanates, diisothiocyanates and the like. They preferably contain 2 to 12 carbon atoms but can also have longer chains. Such an intermediate member can be omitted when the imino-chloride group is reacted directly with a hetero-bifunctional reagent, one function of which is a primary amino group and the other function of which is a protected function which can react with the protein in free form, for example acetal, an ester which can be saponified acidically, hydrogenolytically or weakly basically or an unreactive precursory stage for such a function, for example, a nitrile for imino esters, olefines to epoxides and the like.

The reaction of the imino-chloride with the bi-functional intermediate compound containing at least one amino group takes place in an organic solvent if the intermediate compound (spacer) is itself not liquid; otherwise, it is preferably carried out in the intermediate compound itself as the liquid phase. Reaction in an aqueous medium is also possible since the primary amino group reacts more quickly with the imino-chloride than the OH group. If the primary amino group is bound to an acid amide group, i.e. if it is a hydrazide, then working up is carried out in a solvent, for example dimethyl sulphoxide, formamide or dimethyl formamide. Other strongly polar solvents can, in this case, also be employed.

The process according to the present invention enables the immobilization or fixing of biologically-active proteins on to carrier materials which contain secondary amino groups in the molecule in an especially gentle manner and with the achievement of advantageous properties, especially of surface properties, of these carrier materials. The process can be used not only for the direct coupling of proteins on to the intermediate-formed imino-chloride groups but also for coupling the proteins via intermediate compounds (spacers) which permits the protein molecule to be kept a certain distance from the actual carrier molecule.

The bonding of the protein on to the free function of the bifunctional compound containing at least one primary amino group can, as already mentioned, take place directly or via a further bifunctional protein reagent. The latter serves as a spacer and thus increases the distance between the actual carrier compound and the protein in cases in which it is desired or acts as a protein cross-linking agent which binds together several biologically-active protein molecules and the so obtained cross-linked protein aggregates are then fixed on to the carrier. This fixing can take place via the same polyfunctional protein reagent, via another polyfunctional protein reagent or directly with the second function, capable of protein binding, of the bifunctional compound containing at least one primary amine group. Examples of polyfunctional protein reagents include glutardialdehyde, bis-hydroxysuccinimide esters and other similar compounds which are known in the art. The multifunctional or polyfunctional protein reagent can have two or more functional groups capable of reacting with the protein, appropriate examples of such polyfunctional protein reagents being described, for example, in German Patent Specifications Nos. 2,237,083 and 1,915,970.

This latter embodiment of the present invention is explained in the following Examples 11 and 13. According to Example 11, the biologically-active protein is cross-linked with succinimide ester and thereafter bound by means of glutardialdehyde, as bifunctional protein reagent, on to the free amino group of a diamine which, before reaction with the second primary amino group, has been reacted with the imino-chloride group. Since the succinimide ester is about 100 times more reactive than glutardialdehyde but, on the other hand, is also considerably more expensive, in this manner there can be achieved an increased activity yield but, at the same time, the bonding on to the polymer with the less expensive glutardialdehyde. The simultaneous cross-linking and fixing with a single polyfunctional protein reagent is illustrated in the following Example 13.

According to a further embodiment of the present invention, a carrier surface, for example a fabric, filament, reagent glass or some other desired surface, is provided with an adhesive layer and polyamide chips, flakes or the like are applied thereto by means of an electrostatic covering process. The large surface areas produced in this manner then give, in the case of the protein fixing according to the present invention, a high specific activity per square cm. of covered carrier.

The following Examples are given for the purpose of illustrating the present invention:

EXAMPLES 1 and 2

2 meter lengths of nylon-6 tubing with an internal diameter of 1 mm. are rinsed with anhydrous methanol and subsequently with anhydrous methylene chloride in order to remove traces of moisture. The tubing is then precooled to $-40°$ C. and filled with a 5% solution of phosphorus pentachloride in carbon tetrachloride which has been cooled $-40°$ C. The precise maintenance of the temperature is not critical but temperatures below $-20°$ C. are preferred. After 5 hours, the phosphorus pentachloride solution is sucked out and excess reagent is rinsed out with dry carbon tetrachloride. Ethylenediamine or a 2% solution of oxalic acid dihydrazide in dimethyl sulphoxide is then introduced into the tubing. After standing for 2 hours with the amino or hydrazide solution, the tubing is rinsed overnight with water. The tubing is then rinsed with anhydrous dioxan in order to remove traces of water and a solution of 50 mg. ethylene glycol bis-propionic acid bis-hydroxy-succinimide ester in 2.5 ml. dioxan and 0.5 ml. N-ethylmorpholine is introduced into the tubing. After 30 minutes, the solution is removed by suction and the tubing is rinsed with 0.1 molar triethanolamine buffer (pH 8.5). The tubing is then filled with a solution of 2 mg. glucose dehydrogenase in 1 ml. triethanolamine buffer (pH 8.5) and left to stand for 3 hours at 4° C. It is thereafter rinsed with 5 liters 0.1 molar triethanolamine buffer (pH 8.5) which is 1 molar with regard to sodium chloride. The tubing subsequently displays an activity of 1.5 U/m. (amine tubing) or of 1.6 U/m. (oxalic acid hydrazide tubing).

EXAMPLE 3.

2 meters of nylon-6 tubing are activated as in Example 1. In the case of the enzyme fixing, there is used a solution of 2 mg. glucose oxidase in 1 ml. phosphate buffer (pH 7.8) and the tubing is subsequently rinsed as in Example 1. When testing with a flow through rate of 7 ml./minute, the tubing displays an activity of 1.5 U/m.

EXAMPLE 4.

50 g. nylon-6 granulate are rinsed with anhydrous methanol and subsequently with anhydrous methylene chloride in order to remove traces of moisture. The granulate, pre-cooled to $-40°$ C., is mixed with a 5% solution of phosphorus pentachloride in carbon tetrachloride cooled to $-40°$ C. and stirred. After stirring for 5 hours at $-40°$ C., the granulate is filtered off with suction and excess reagent is washed out with dry carbon tetrachloride. The granulate is then mixed with a 20% solution of hexamethylenediamine in methanol and, after 2 hours, filtered off with suction. Subsequently, the granulate is packed into a column and rinsed overnight with water. The granulate is then stirred for 12 minutes with a 10% solution of glutardialdehyde in 0.2 molar borate buffer (pH 8.5). Subsequently, it is filtered off with suction and rinsed with 0.1 molar phosphate buffer (pH 7.8). 10 g. of the activated granulate are then mixed with a solution of 80 mg. glucose oxidase in 40 ml. 0.1 molar phosphate buffer (pH 7.8) and stirred for 3 hours at 4° C. The granulate is subsequently packed into a column and washed with 0.1 molar phosphate buffer (pH 7.8) which is 1 molar with regard to sodium chloride. The granulate subsequently displays an activity of 240 U/g.

EXAMPLE 5.

2 meters of nylon tubing with an internal diameter of 1 mm. are cooled to −30° C. and filled with a 10% solution of phosphorus pentachloride in carbon tetrachloride which has been cooled to −30° C. After 5 hours, the tubing is rinsed with dry methylene chloride and immediately afterwards filled with an aqueous solution of glucose oxidase with a concentration of 5 mg. glucose oxidase/ml. of 0.3 molar TRA buffer (pH 8.0). After 3 hours at 4° C., the tubing is rinsed with a 1 molar solution of sodium chloride in 0.1 molar phosphate buffer (pH 7.0). The activity of the glucose-oxidase tubing thus produced is about 0.15 U/m. when tested at a flow through rate of 7 ml./minute.

EXAMPLE 6.

2 meters of nylon tubing are activated in the manner described in Example 1. As spacer, there is employed succinic acid hydrazide (0.3% solution in dimethyl sulphoxide) and as bifunctional protein reagent glutardialdehyde. For fixing, a solution of 2 mg. glycerokinase in 1 ml. phosphate buffer (pH 7.8) is employed and the tubing is subsequently rinsed as in Example 1. When the tubing is tested with a flow through rate of 7 ml./minute, it displays an activity of 0.4 U/m.

EXAMPLE 7.

5 g. nylon-6 granulate are suspended in 20 ml. carbon tetrachloride. Phosgene is then bubbled through the suspension at ambient temperature for 25 minutes. Subsequently, the nylon granulate is washed with carbon tetrachloride and the nylon polyiminochloride obtained is mixed with a solution of 10 mg. glucose oxidase in 10 ml. 0.1 molar phosphate buffer (pH 7.8). After washing in the manner described in Example 4, the granulate displays an activity of 50 U/g.

EXAMPLE 8.

10 g. polyamide-6 powder are introduced, with cooling, into 40 ml. benzene in which are dissolved 8.4 g. phosphorus pentachloride and the temperature then maintained overnight at 4° C. Then, without isolation of the reactive imino-chloride intermediate product, into the same batch is introduced a solution of 2.4 g. hexamethylenediamine in 20 ml. benzene and the batch is boiled under reflux for 2 hours. Thereafter, the powder is filtered off with suction, subsequently washed with othanol and, after briefly washing with distilled water, 0.5 g. of the activated derivative are added to 1 ml. of a solution of 20 mg. glucose oxidase in 1 ml. 0.1 molar phosphate buffer (pH 7.8). After leaving to stand overnight at 4° C., the powder is washed with 0.1 molar phosphate buffer (pH 7.0) which is 1 molar with regard to sodium chloride. In the case of the fixed glucose-oxidase-nylon derivative thus obtained, there is ascertained an activity of 41 U/g., corresponding to 25 U/ml. packing volume.

EXAMPLE 9.

10 g. polyamide-6 powder are reacted, in the manner described in Example 8, with a solution of phosphorus pentachloride and subsequently reacted with a solution of hexamethylenediamine. For the liberation of the second amino group of the condensed on diamine, the material is subsequently briefly washed with a 0.5N aqueous solution of sodium hydroxide and the product is then washed free of hydroxyl ions and thereafter mixed for 15 minutes with a 10% solution of glutardialdehyde in 0.2 M borate buffer (pH 8.5). After further washing with distilled water, 5 g. of the activated nylon product are mixed with 5 ml. of a solution of 20 mg. glucose oxidase/ml. 0.1M phosphate buffer (pH 7.8). After standing overnight at 4° C., the product is filtered off with suction and washed with 0.1M phosphate buffer (ph 7.8) which is 1M with regard to sodium chloride. The activity of the fixed glucose oxidase amounts to 78 U/g., corresponding to 48 U/ml. packing volume.

EXAMPLE 10.

30 g. nylon-6 are dissolved in 100 ml. formic acid. 10 g. of clay particles with a diameter of 0.315 to 0.400 mm. are mixed with this solution so that the pores of the particles are filled with the nylon solution but discrete individual particles are still present. After stripping off the formic acid in a vacuum, the particles are washed with an aqueous solution of sodium bicarbonate, washed neutral with distilled water and the product, after drying, reacted as in Example 9 with phosphorus pentachloride solution and hexamethylenediamine solution, briefly washed with 0.5N aqueous sodium hydroxide solution, then washed neutral and thereafter reacted with a 5% solution of a co-polymer of acrylic acid hydroxysuccinimide ester and acrylamide at a pH of 7.8 for 4 hours. A degassing of the particles gives a better reaction with the dissolved co-polymer. Thereafter, the particles are washed with distilled water and 1 g. of the clay particles are mixed with 2 ml. of a solution of 5 mg. glucose oxidase/ml. 0.1M phosphate buffer (pH 7.8). After standing overnight at 4° C., the particles are filtered off with suction and washed with phosphate buffer (pH 7.0) which is 0.1M with regard to sodium chloride. The particles display an activity of 14 U/g., corresponding to 15 U/ml. of packing volume.

EXAMPLE 11

In a mixture of 18.6 g. calcium chloride and 18.6 g. water, together with 63 g. methanol and 1 to 1,000 parts of formic acid, polyamide is dissolved at an elevated temperature of 30° to 80° C. and filled, while hot, into a 2 meter long nylon-6 tubing and thereafter immediately rinsed with cold water. On the inner surface of the tubing there remains a coating of amorphous, reactive nylon. The tubing is washed free of water with dry methanol and left to stand overnight in a 5% solution of phosphorus pentachloride in chloroform at 4° C. Thereafter, a 20% solution of hexamethylenediamine in methanol is introduced into the tubing and after one hour it is washed with 5 litres of distilled water. A 10% solution of glutardialdehyde in 0.2M borate buffer (pH 8.5) is then introduced and, after 15 minutes, the tubing is washed with 0.1M phosphate buffer (pH 7.8). In the meantime, 372 mg. glucose oxidase are dissolved in 4.5 ml. 0.1M phosphate buffer (pH 7.8) and mixed with 6.4 mg. ethylene-glycol bis-propionic acid bis-hydroxy-succinimide ester in 0.5 ml. dioxan and left to stand overnight at 4° C. This glucose oxidase solution is diluted 1:4 and the cross-linked glucose oxidase product filled into the nylon tubing. After washing the tubing with 0.1M phosphate buffer (pH 7.0) which is 1M with regard to sodium chloride, 50 cm. long pieces are tested at a flow through rate of 7 ml./minute. Under these test conditions, there are obtained activities of 5, 7.5 and 9 U/m. (in 3 batches).

EXAMPLE 12

A Tygon tubing is briefly partly dissolved with cyclohexanone. A nylon solution prepared as in Example 11 is then introduced and the tubing further worked up as in Example 11. Upon testing, there is obtained an activity of 3 U/m.

EXAMPLE 13

A nylon tubing is treated with a nylon solution as in Example 11 and subsequently with a solution of phosphorus pentachloride and a solution of hexamethylenediamine. After washing with 5 litres distilled water in a manner analogous to that described in Example 11, there is introduced a 5% solution of a co-polymer of methacrylic acid hydroxysuccinimide ester and methacrylamide at pH 7.8. After 4 hours, the tubing is washed with distilled water and a solution of 2 mg. glucose oxidase/ml. 0.1M phosphate buffer (pH 7.8) is introduced and the tubing left to stand overnight at 4° C. After washing with 0.1M phosphate buffer (pH 7.0), which is 1M with regard to sodium chloride, there is obtained, in the case of testing 50 cm. pieces at a flow through rate of 7 ml./minute, an activity of 2.4 U/m.

It will be understood that the specification and examples are illustrative but not limitative of the present invention and that other embodiments within the spirit and scope of the invention will suggest themselves to those skilled in the art.

What is claimed is:

1. Process for immobilizing biologically-active proteins onto a carrier material, which process comprises reacting a compound containing at least two secondary amino groups at a temperature of from $-80°$ to $+50°$ C. with a chlorination agent with the conversion of the secondary amino groups into iminochloride groups of the formula $$R-\underset{Cl}{C}=N-R_1$$

in which R and $R_1$, which can be the same or different, are aliphatic, aromatic or aliphatic-aromatic radicals, and reacting the carrier material product thus obtained
(a) directly with a biologically-active protein, in an aqueous solvent, or
(b) with a bifunctional compound containing at least one primary amino group, optionally in an aqueous or organic solvent, and reacting the product thereby obtained containing groups of the formula $$R-\underset{NH-R_2-X}{C}=N-R_1$$

in which $R_2$ is an alkylene radical, an $\alpha,\omega$-dioxyalkylene radical or a dicarboxylic acid amide group containing 2 to 8 carbon atoms and X is a primary amino group or a function capable of protein binding either
(i) directly with a protein or
(ii) first with at least one bifunctional or polyfunctional protein reagent and thereafter with a protein or with a reaction product of a protein with the protein reagent.

2. Process as claimed in claim 1 wherein said compound containing at least two secondary amino groups is a solid polymer.

3. Process as claimed in claim 2 wherein said solid polymer is a polyamide.

4. Process as claimed in claim 1 where said compound containing at least two secondary amino groups is a protein.

5. Process as claimed in claim 1 wherein said chlorination agent is selected from phosphorous pentachloride, phosphorous trichloride, thionyl chloride, phosgene, phosphourus oxychloride or sulfuryl chloride.

6. Process as claimed in claim 1 wherein R and $R_1$ contain at least one member of the group consiting of secondary amino groups, tertiary amino groups, ester groups, amide groups, sulfhydryl groups, carboxyl groups, hydroxyl groups and imino-chloride groups.

7. Process as claimed in claim 6 wherein R and $R_1$ are selected from straight-chained, branched and cyclic alkyl or alkylene radicals containing up to 12 carbon atoms, phenyl radicals or phenylene radicals or alkylphenyl radicals or alkylphenylene radicals containing up to 6 carbon atoms in the alkyl radical, which are joined together by one or more secondary or tertiary amino groups, ester groups, amide groups and iminochloride groups.

8. Process as claimed in claim 1 wherein X is selected from acetal groups, ester groups, nitrile groups and olefinic groups.

9. Process as claimed in claim 1 wherein the bifunctional protein reagent is selected from dialdehydes, dihydroxysuccinimide esters, diacetal, bis-maleinimides, bifunctional imino esters, diepoxide and dicarboxylic aids, dichlorides, diisocyanate and diisothiocyanates.

10. Process as claimed in claim 1 wherein the surface of said carrier material is covered with polyamide chips, fibers or flakes.

11. Immobilized biologically active proteins prepared by the process as claimed in claim 1.

12. Process as claimed in claim 1 wherein said carrier material product obtained in reacted directly with a biologically active protein, in an aqueous solvent.

13. Process as claimed in claim 1 which comprises reacting said carrier material product obtained with a bifunctional compound containing at least one primary amino group, and then reacting the product thereby obtained, containing groups of the formula $$R-\underset{NH-R_2-X}{C}=N-R_1$$

in which $R_2$ is an alkylene radical, an $\alpha,\omega$-dioxyalkylene radical or a dicarboxylic acid amide group containing 2 to 8 carbon atoms and X is a primary amino group or a function capable of protein binding, either
(i) directly with a protein or
(ii) first with at least one bifunctional or polyfunctional protein reagent and thereafter with a protein or with a reaction product of a protein with the protein reagent.

* * * * *